(12) United States Patent
Izumi et al.

(10) Patent No.: US 8,663,119 B2
(45) Date of Patent: Mar. 4, 2014

(54) WRIST SPHYGMOMANOMETER

(75) Inventors: Tomohiro Izumi, Osaka (JP); Fumuro Shinichi, Hikone (JP); Akihiro Mizuuchi, Hikone (JP)

(73) Assignee: Panasonic Corporation, Osaka (JP)

( * ) Notice: Subject to any disclaimer, the term of this patent is extended or adjusted under 35 U.S.C. 154(b) by 449 days.

(21) Appl. No.: 12/984,784

(22) Filed: Jan. 5, 2011

(65) Prior Publication Data

US 2011/0172547 A1    Jul. 14, 2011

(30) Foreign Application Priority Data

Jan. 8, 2010    (JP) ................................. 2010-002787

(51) Int. Cl.
*A61B 5/02*    (2006.01)

(52) U.S. Cl.
USPC .......................................... 600/490; 600/500

(58) Field of Classification Search
None
See application file for complete search history.

(56) References Cited

U.S. PATENT DOCUMENTS

| | | | | |
|---|---|---|---|---|
| 5,172,696 | A | * | 12/1992 | Souma .......................... 600/473 |
| 5,316,008 | A | | 5/1994 | Suga et al. |
| 6,126,595 | A | | 10/2000 | Amano et al. |
| 6,712,769 | B2 | | 3/2004 | Freund et al. |
| 2003/0181816 | A1 | * | 9/2003 | Shirasaki ....................... 600/490 |
| 2004/0077958 | A1 | | 4/2004 | Kato et al. |
| 2008/0300495 | A1 | * | 12/2008 | Yang et al. .................... 600/494 |
| 2010/0249615 | A1 | | 9/2010 | Kukita et al. |
| 2011/0224561 | A1 | * | 9/2011 | Ashida .......................... 600/493 |
| 2011/0245695 | A1 | * | 10/2011 | Kawano et al. ............... 600/493 |

FOREIGN PATENT DOCUMENTS

| | | |
|---|---|---|
| CN | 1158077 A | 8/1997 |
| CN | 1400882 A | 3/2003 |
| CN | 2762755 Y | 3/2006 |
| EP | 1647222 A1 | 4/2006 |
| EP | 1405592 A1 | 4/2007 |
| EP | 1870036 A1 | 12/2007 |
| JP | 3-147067 | 6/1991 |
| JP | 4-200439 | 2/1992 |
| JP | 07-143970 | 6/1995 |

(Continued)

OTHER PUBLICATIONS

Office Action received in corresponding Japanese Patent Application No. JP2010-002787.
Office Action received in corresponding Japanese Patent Application No. JP2007-54648.

(Continued)

*Primary Examiner* — Michael Kahelin
*Assistant Examiner* — Tho Tran
(74) *Attorney, Agent, or Firm* — Wolf, Greenfield & Sacks, P.C.; Randy J. Pritzker (57) ABSTRACT

A wrist sphygmomanometer includes an operation unit operable by a user. A manometer measures blood pressure. A detector detects the posture of the user. A storage stores an optimum posture for the user. A comparator compares the posture detected by the detector and the optimum posture stored beforehand in the storage to generate posture information. A communication unit communicates the posture information to the user. A setting unit sets the optimum posture in the storage. The storage includes a first storage section, which stores a fixed optimum posture corresponding to an unspecified user, and a second storage section, which stores a second optimum posture corresponding to a specified used. The setting unit stores the second posture based on a value detected by the detector as the second optimum posture in the second storage section in accordance with an operation of the operation unit.

9 Claims, 4 Drawing Sheets

(56) References Cited

FOREIGN PATENT DOCUMENTS

| JP | 2006-065752 | 3/2006 | | |
|---|---|---|---|---|
| JP | 2007-054648 A | 3/2007 | | |
| JP | 2009-189485 | 2/2009 | | |
| JP | 2009-112521 | 5/2009 | | |
| JP | 2009-247733 | 10/2009 | | |
| WO | WO2006/124768 | * 11/2006 | ............. | A61B 5/103 |
| WO | WO 2006/124768 A1 | 11/2006 | | |

OTHER PUBLICATIONS

Office Action in corresonding Chinese application No. 201010624583.7, dated Sep. 7, 2012, pp. 1-9 (translation of office action Summary, pp. 1-6).

Office Action from corresponding European patent application 10 197 107.5-1657 dated Mar. 12, 2013, pp. 1-5.

* cited by examiner

__WRIST SPHYGMOMANOMETER__

CROSS-REFERENCE TO RELATED APPLICATIONS

This application is based upon and claims the benefit of priority from prior Japanese Patent Application No. 2010-002787, filed on Jan. 8, 2010, the entire contents of which are incorporated herein by reference.

BACKGROUND OF THE INVENTION

The present invention relates to a wrist sphygmomanometer for attachment to a wrist to measure blood pressure.

A wrist sphygmomanometer includes a measurement means, which measures the blood pressure, and a display, which displays the blood pressure measured by the measurement means. Japanese Laid-Open Patent Publication No. 2007-54648 describes an example of such a wrist sphygmomanometer that includes a detection means, which detects the posture of the user whose blood pressure is to be measured, and a comparison means, which compares the posture detected by the detection means with an optimum posture stored in a storage means. The wrist sphygmomanometer uses, for example, visual graphics that are easy to understand to guide the user to the optimum posture. When the user measures the blood pressure in the optimum posture (or tolerable range), the accuracy for measuring the blood pressure is improved. Further, in the wrist sphygmomanometer of the publication, after initialization is completed but before the user's posture is detected, the user uses an operation unit to input user information (biological information such as the forearm length or the upper arm length). This allows for correction of the biological information in accordance with each individual. Thus, the measurement accuracy is further improved.

In the wrist sphygmomanometer described above, however, after initialization is completed but before the user's posture is detected, the task performed with the operation unit to input the user information (biological information) is burdensome. Further, the wrist sphygmomanometer may be used by a specified user (i.e., the owner) or an unspecified user. Thus, it is desirable that the sphygmomanometer be user-friendly regardless of the user.

SUMMARY OF THE INVENTION

The present invention provides a sphygmomanometer that is user-friendly regardless of the user.

One aspect of the present invention is a wrist sphygmomanometer attachable to a user's wrist. The wrist sphygmomanometer includes an operation unit operable by the user. A manometer measures blood pressure. A detector detects the posture of the user. A storage stores an optimum posture for the user. A comparator compares the posture detected by the detector and the optimum posture stored beforehand in the storage to generate posture information. A communication unit communicates the posture information to the user. A setting unit sets the optimum posture in the storage. The storage includes a first storage section, which stores a fixed optimum posture corresponding to an unspecified user, and a second storage section, which stores a second optimum posture corresponding to a specified user. The setting unit stores a value based on the posture detected by the detector as the second optimum posture in the second storage section in accordance with an operation of the operation unit.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE INVENTION

A sphygmomanometer 1 according to one embodiment of the present invention will now be discussed in accordance with FIGS. 1 to 7.

Figure 1:
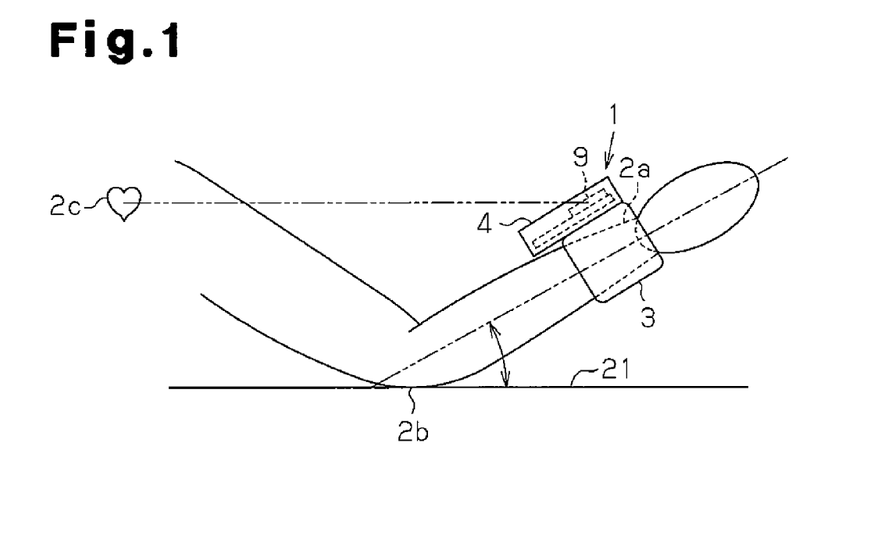
FIG. 1 is a schematic diagram showing a wrist sphygmomanometer according to one embodiment of the present invention in a state attached to a wrist.

As shown in FIG. 1, the wrist sphygmomanometer 1 includes a cuff 3 and a main body 4. The cuff 3 is placed around a user's wrist 2a. The main body 4 is coupled to the cuff 3.

Figure 2:
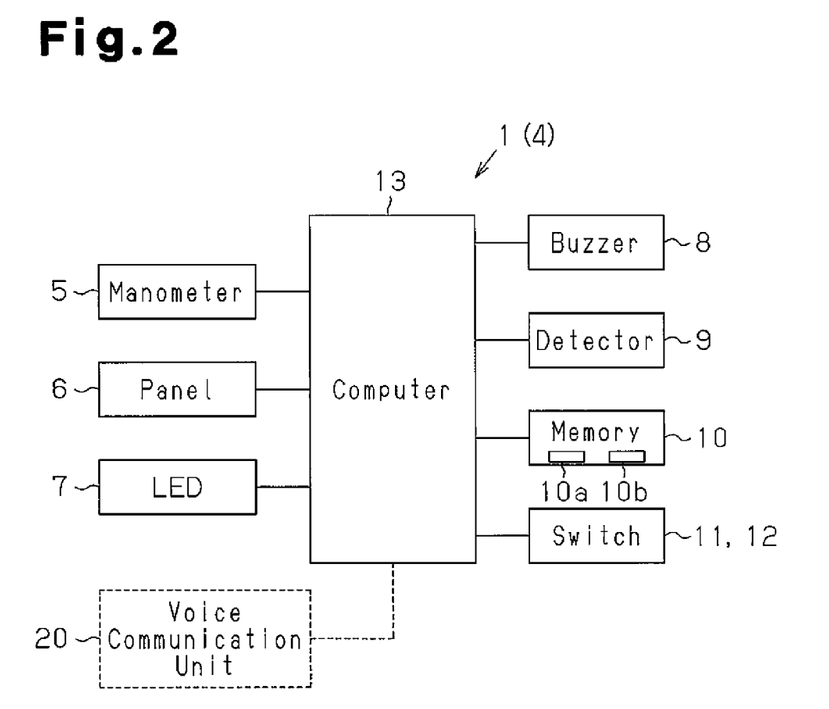
FIG. 2 is a schematic block diagram of the wrist sphygmomanometer shown in FIG. 1.
Figure 3A:
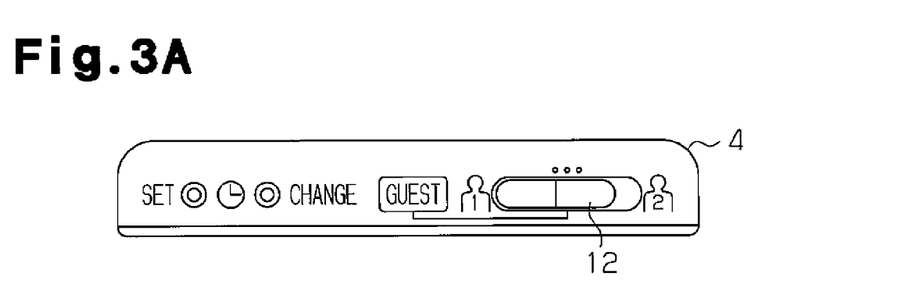
FIG. 3A is a side view of the sphygmomanometer shown in FIG. 1.
Figure 3B:
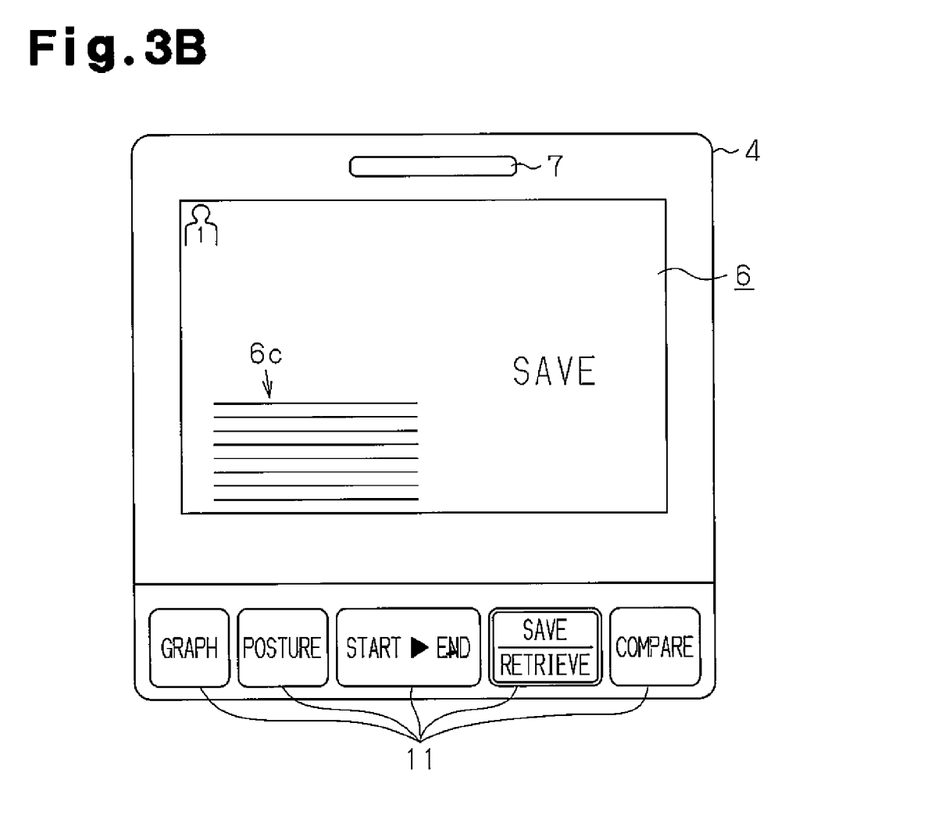
FIG. 3B is a front view of the sphygmomanometer shown in FIG. 1.

Referring to FIGS. 2 and 3, the main body 4 includes a manometer 5, a liquid crystal panel 6, a detector 9, a memory 10, push button switches 11, a selection switch 12, and a computer 13. The manometer 5 measures the blood pressure. The liquid crystal panel 6 serves as a display unit and a communication unit. The detector 9 detects the posture of the user. The memory 10 serves as a storage. The computer 13 serves as a comparator and a setting unit. The switches 11 and 12 form an operation unit. The switches 11 and 12 are separated in accordance with function. The selection switch 12 may also be formed by a push button switch. Further, the main body 4 includes a light emitting diode (LED) 7 and a buzzer 8.

The manometer 5 includes a pressurizing unit, which controls the air in the cuff 3 for pressurizing and depressurizing, and a sensor, which detects the flow of blood, and measures the blood pressure using the pressurizing unit and the sensor. In the present embodiment, the manometer 5 is capable of measuring the pulse rate in addition to the blood pressure.

As shown in FIG. 3B, the liquid crystal panel 6 is arranged in the front surface of the main body 4 that is opposite to a surface to which the cuff 3 is attached. This makes sure the liquid crystal panel 6 is easily viewable for a user. The liquid crystal panel 6 includes a seven-segment type blood pressure display 6a (refer to FIG. 6), which displays numerals that show the results of the blood pressure measured by the manometer 5. Further, the liquid crystal panel 6 includes a seven-segment type pulse rate display 6b, which displays the measurement result of the pulse rate at the same time as when the blood pressure measurement result is displayed.

The liquid crystal panel 6 also includes a display 6c (FIGS. 4 to 7), which includes an array or matrix of dots, i.e., a plurality of dots. In the present embodiment, the dot matrix display 6c includes eight rows and eight columns of dots totaling to an array of 64 dots. The dot matrix display 6c is capable of graphically displaying blood pressure measurement results (including values computed from the measurement results) (refer to FIGS. 6 and 7). Further, the dot matrix display 6c is capable of displaying guidance information using graphics or the like (refer to FIGS. 4 and 5). The guidance information serves as posture information.

As shown in FIG. 3B, the LED 7 is arranged in the front surface of the main body 4 above the liquid crystal panel 6.

The buzzer 8 oscillates and generates an electronic sound, such as a beep, when a switch 11 is pushed or in synchronism with the pulses measured by the manometer 5.

The detector 9 detects the posture of the user. In the present embodiment, the detector 9 includes an acceleration sensor (angle sensor) and detects the height from a plane 21, on which the user's arm is resting, to the main body 4 (wrist 2a) as the user's posture.

The memory 10 is used as an optimum posture storage, which stores the optimum posture of a user, but is also capable of storing other types of data. In the present embodiment, the location of a user's wrist in a predetermined range corresponding to the height of the user's heart 2c is stored as the optimum posture. Further, the memory 10 includes a first storage section 10a and a second storage section 10b. The first storage section 10a stores a first optimum posture, which is fixed and corresponds to an unspecified user. The second storage section 10b stores a second optimum posture, which corresponds to a specified user. In the present embodiment, the second storage section 10b is capable of storing the second optimum posture separately for two individuals serving as specified users. When the selection switch 12 (refer to FIG. 3A) is shifted to the left, the computer 13 accesses the second storage section 10b. This allows for the computer 13 to save (store) and read the second optimum posture corresponding to a first specified user denoted by the numeral of "1". When the selection switch 12 (refer to FIG. 3A) is shifted to the right, the computer 13 accesses the second storage section 10b. This allows for the computer 13 to save (store) and read the second optimum posture corresponding to a second specified user denoted by the numeral of "2". As shown in FIG. 3A, the selection switch 12 may be shifted to three positions, namely, left, middle, and right positions. When the selection switch 12 is located at the middle position, the computer 13 accesses the first storage section 10a. This allows for the computer 13 to read the first optimum posture corresponding to an unspecified user. The first optimum posture is set beforehand as a fixed value.

The memory 10 also functions as a result storage that stores posture determination information, which shows the result of a comparison between the optimum posture and the posture detected by the detector 9, in association with the result of the blood pressure measured by the manometer 5.

The computer 13, which includes a microprocessor unit (MPU) and a driver for driving the liquid crystal panel 6, performs various computations and processes.

The operation procedures for the wrist sphygmomanometer 1 of the present embodiment will now be discussed.

When a specific user, such as an owner, uses the wrist sphygmomanometer 1, the optimum posture for the specific user (second optimum posture) is stored as described below.

First, referring to FIG. 1, when the user's wrist 2a (main body 4) is arranged at the same height as the user's heart 2c, the switch 11 marked by "POSTURE" (refer to FIG. 3B) and serving as an operation unit is operated (for example, continuously pushed for two seconds). As a result, the computer 13, which serves as the setting unit, stores a value corresponding to the posture detected by the detector 9 as the second optimum posture in the second storage section 10b. The second optimum posture stored in the second storage section 10b has a tolerable range so that the wrist 2a (main body 4) may be moved slightly upward or downward from the position of the posture detected by the detector 9. The tolerable range is set to be narrower than the tolerable posture range of the first optimum posture. In other words, the tolerable posture range for the fixed first optimum posture is widely set so as to be applicable to an unspecified user. When the second optimum posture is stored in the present embodiment, as shown in FIG. 3B, the computation displays the characters of "SAVE" on the liquid crystal panel 6. FIG. 3B shows a state in which the selection switch 12 (refer to FIG. 3A) is shifted to the left position. Thus, the second optimum posture corresponding to the first specific user denoted by the numeral of "1" is saved (set).

Next, the operations performed when the user measures the blood pressure will be discussed.

In this case, the user operates (pushes) the switch 11 marked by "START▶ END" (refer to FIG. 3B). As a result, the computer 13, which serves as a comparator, compares the posture detected by the detector 9 with the optimum posture (first or second optimum posture), which is stored beforehand, to generate posture information based on the comparison. The posture information of the present embodiment includes posture determination information, which indicates whether or not the posture detected by the detector 9 differs from the optimum posture, and guidance information, which advises the user to move the user's wrist 2a (main body 4) upward or downward so that the user's posture approaches the optimum posture. The selection switch 12 (refer to FIG. 3A) is operated to switch the optimum posture that is subject to comparison, namely, the first optimum posture, which corresponds to an unspecified user (GUEST), and the second optimum posture, which corresponds to the first user ("1") when the selection switch 12 is located at the left position and the second user ("2") when the selection switch 12 is located at the right position.

Figure 4:
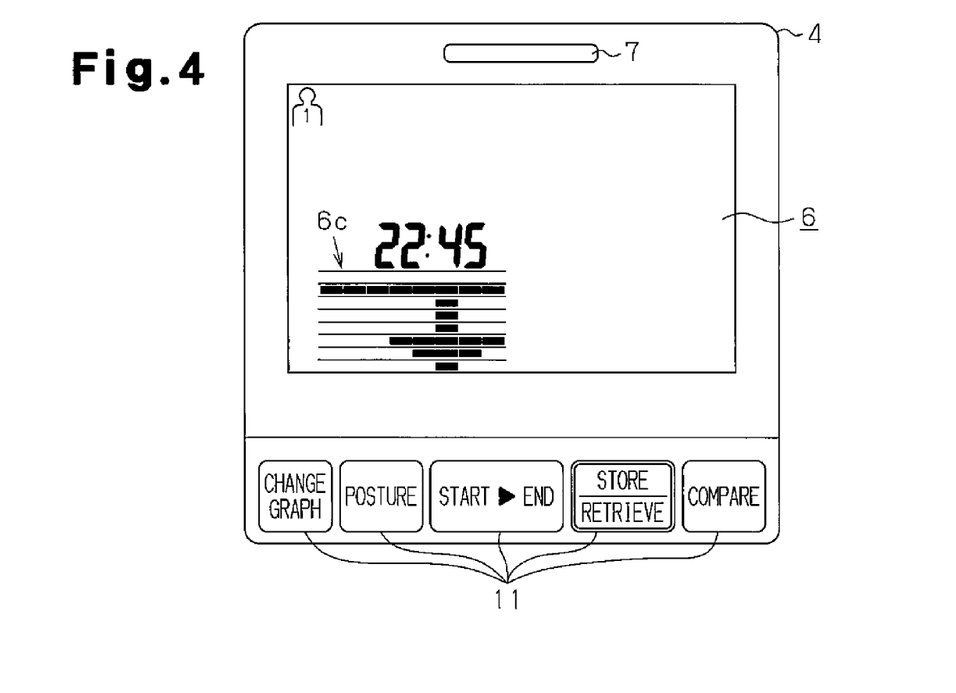
FIG. 4 is a front view of a main body of the sphygmomanometer shown in FIG. 1.
Figure 5:
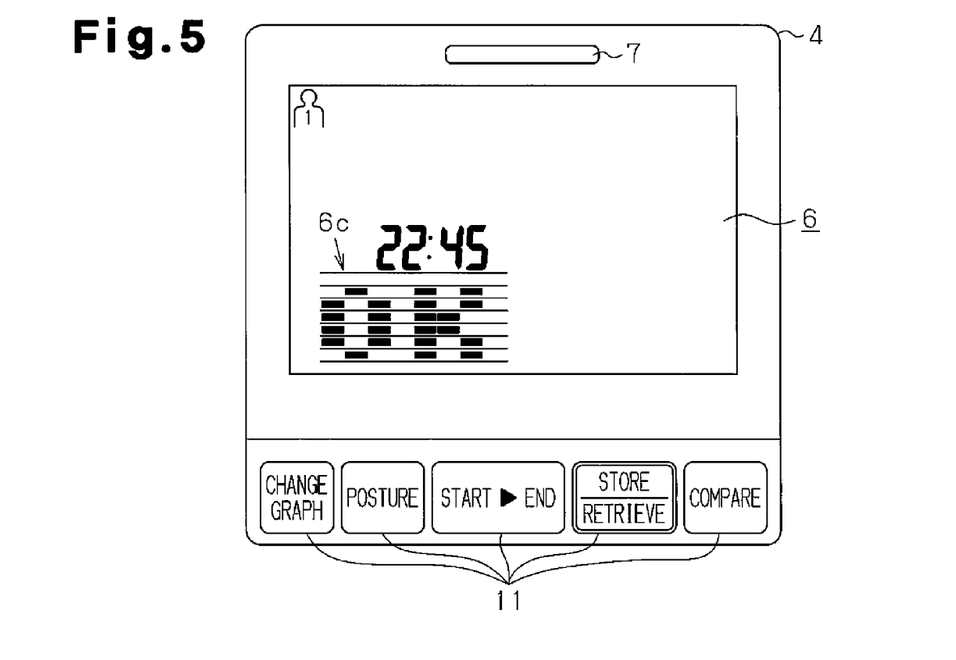
FIG. 5 is a front view of the main body of the sphygmomanometer shown in FIG. 1.

The computer 13 communicates the posture information to the user with the communication unit. In the present embodiment, the communication unit includes the dot matrix display 6c of the liquid crystal panel 6. Thus, the dot matrix display 6c is capable of displaying the posture information in addition to the measurement result of the blood pressure. For example, in a state in which the posture detected by the detector 9 differs from the optimum posture (outside the tolerable posture range of the optimum posture), when downward movement of the wrist 2a would lead to the user's posture approaching the optimum posture, the dot matrix display 6c communicates such guidance information by displaying the graphic of a downwardly directed arrow, as shown in FIG. 4. On the other hand, when upward movement of the wrist 2a would lead to the user's posture approaching the optimum posture, the dot matrix display 6c communicates such guidance information by displaying the graphic of an upwardly directed arrow (not shown). Further, when the posture detected by the detector 9 conforms to the optimum posture (i.e., the tolerable posture range of the optimum posture), the dot matrix display 6c communicates such information by displaying, for example, the characters of "OK" as shown in FIG. 5. In this case, the dot matrix display 6c may also repetitively exhibit or illuminate the dots to display the posture information (guidance information). Such repetitive exhibition or illumination includes simple flashing of a graphic, such as an arrow, and animation produced by shifting the exhibited or illuminated dots, for example, in an upward or downward direction.

A device other than the dot matrix display 6c may serve as the communication unit, which communicates the posture information to the user. For example, the LED 7 of the present embodiment serves as an auxiliary communication unit. In other words, the dot matrix display 6c and the LED 7 each function as a communication unit. For instance, when the posture detected by the detector 9 conforms to the optimum posture and is included in the tolerable posture range of the optimum posture, the LED 7 may be illuminated to communicate such posture information. The illumination of the LED 7 would allow the user to recognize that the present posture is the optimum posture. On the other hand, when the posture detected by the detector 9 differs from the optimum posture and is not included in the tolerable posture range of the optimum posture, the LED 7 may be flashed to communicate such posture information. Accordingly, the flashing of the LED 7 would allow the user to recognize that the present posture differs from the optimum posture.

When the posture detected by the detector 9 conforms to the optimum posture and is included in the tolerable posture range of the optimum posture, the computer 13 starts measuring the blood pressure. When the posture detected by the detector 9 differs from the optimum posture, the computer 13 repeats the process for communicating the posture determination information or guidance information with the communication unit. When a predetermined time (e.g., seven seconds) elapses but the posture detected by the detector 9 still does not conform to the optimum posture, the computer 13 may start measuring the blood pressure with the manometer 5 even though the detected posture differs from the optimum posture.

Figure 6:
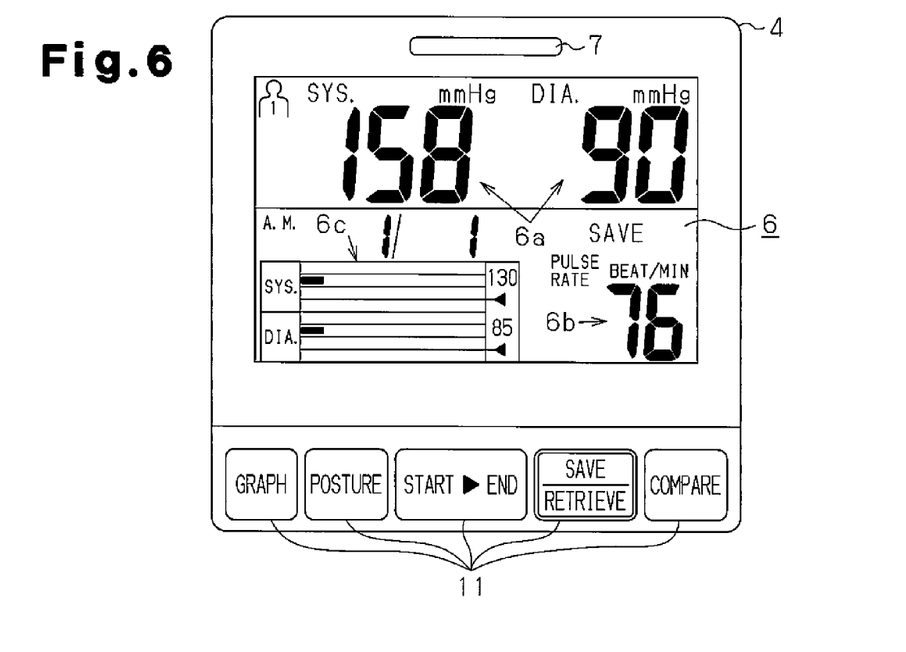
FIG. 6 is a front view of the main body of the sphygmomanometer shown in FIG. 1.

When the blood pressure and pulse rate are measured by the manometer 5, the computer 13 shows the measurement results on the liquid crystal panel 6 by displaying the blood pressure on the blood pressure display 6a and the pulse rate on the pulse rate display 6b, as shown in FIG. 6. Further, the computer 13 shows the measurement result of the blood pressure in a graph on the dot matrix display 6c of the liquid crystal panel 6.

The computer 13 stores the measurement results of the blood pressure and pulse rate together with the date and time of measurement in the memory 10. The computer 13 also stores the posture determination information, which indicates the result of the comparison of the posture detected by the detector 9 and the optimum posture, in association with the result of the blood pressure measured by the manometer 5 in the memory 10 (result storage). As described above, the posture determination information is generated by the computer when starting (or just before starting) measurement with the manometer 5 and indicates the determination result of whether or not the posture detected by the detector 9 differs from the optimum posture.

The result of the blood pressure measured by the manometer 5 is displayable, for example, in various patterns at later dates.

For instance, when a switch 11 is operated, the wrist sphygmomanometer 1 may display a single blood pressure measurement result obtained in the past. In this case, the wrist sphygmomanometer 1 simultaneously displays the blood pressure measurement result and the posture determination information (i.e., the determination result of whether or not the posture detected by the detector 9 differs from the optimum posture) on the liquid crystal panel 6 and the LED 7. In the present embodiment, the liquid crystal panel 6 and the LED 7 form a simultaneous display unit. More specifically, if the posture detected by the detector 9 when starting measurement conformed to the optimum posture, the computer 13 lights or illuminates the LED 7 while displaying the blood pressure measurement result on the blood pressure display 6a of the liquid crystal panel 6. In this manner, the computer 13 simultaneously communicates the blood pressure measurement result and the posture determination information, which indicates that the measurement was performed in the optimum posture. Instead of or in addition to illuminating the LED 7, the dot matrix display 6c may display the posture determination information using, for example, the characters of "OK". If the posture detected by the detector 9 when starting measurement differed from the optimum posture, the computer 13 flashes the LED 7 while displaying the blood pressure measurement result on the blood pressure display 6a of the liquid crystal panel 6. In this manner, the computer 13 simultaneously communicates the blood pressure measurement result and the posture determination information, which indicates that the measurement was not performed in the optimum posture. Further, instead of or in addition to flashing the LED 7, the dot matrix display 6c may display the posture determination information using, for example, the characters of "NG".

Figure 7:
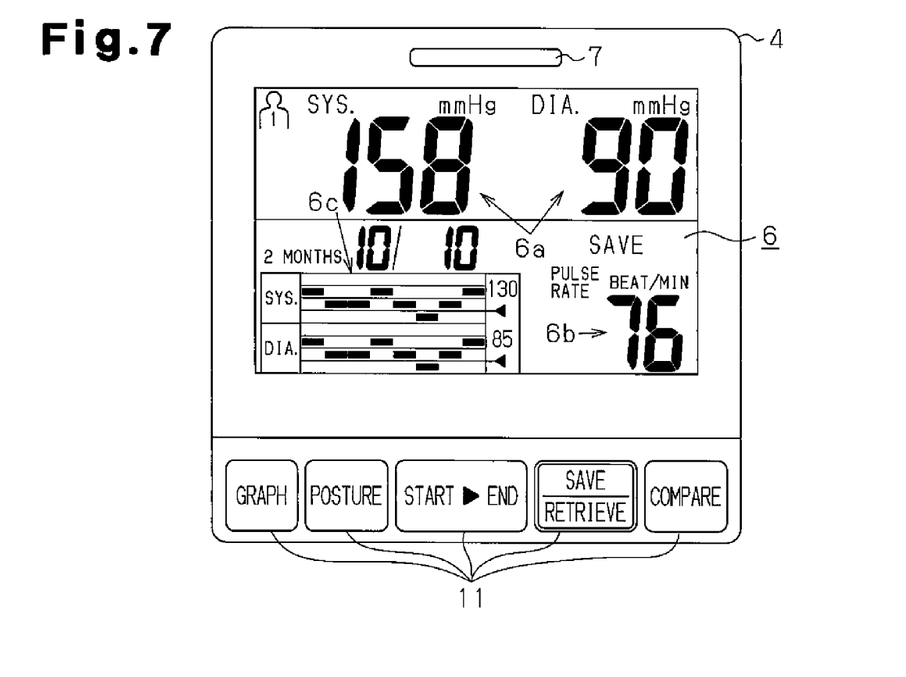
FIG. 7 is a front view of the main body of the sphygmomanometer shown in FIG. 1.

When a switch 11 is operated, the computer 13 may use a plurality of blood pressure measurement results obtained in the past to perform a computation and display the computation result on a display. For example, the computer 13 may compute an average value of a plurality of blood pressure measurement results. In such a case, it is preferable that the computer 13 perform the computation based on the posture determination information. For example, when computing the average blood pressure, the computer 13 may exclude blood pressure measurement results obtained when the posture detected by the detector 9 differed from the optimum posture. Further, the computer 13 may compute the average values for plural types of blood pressure measurement results. In such a case, the dot matrix display 6c functions as an average value simultaneous display unit and simultaneously displays the averages values for the plural types of blood pressure measurement results. For example, as shown in FIG. 7, the computer 13 may compute the average blood pressure (excluding values obtained when the posture was not optimum) for each week during a period of eight weeks (about two months). Then, the computer 13 simultaneously displays the computation results for each week in a graph from left to right in the dot matrix display 6c. The average value for plural types of blood pressures may be, for example, an average value for certain periods of time, such as only the morning.

The above-discussed embodiment has the advantages described below.

(1) The memory 10 (optimum posture storage), which stores optimum postures, includes the first storage section 10a, which stores the fixed first optimum posture that corresponds to an unspecified user, and the second storage section 10b, which stores the second optimum posture that corresponds to a specified user. When a switch 11 (operation unit) is operated, the computer 13 (setting unit) stores a value based on the posture of the user detected by the detector 9 as the second optimum posture in the second storage 10b. Thus, there is no need to manually input the second optimum posture (the values thereof or the like), and the storage of the second optimum posture that corresponds to a specific user is simplified. As a result, highly accurate posture information, which is based on the comparison of the posture detected by the detector 9 and the second optimum posture, is communicated to the user. Further, posture information based on the comparison of the posture detected by the detector 9 and the fixed first optimum posture stored beforehand may be communicated to an unspecified user. In this manner, posture information is easily communicated not only to a specified user but also to an unspecified user. Moreover, the fixed first optimum posture, which is stored beforehand in the first storage section 10*a*, is used for an unspecified user. Thus, an unspecified user may skip the process for setting the optimum posture and immediately measure the blood pressure.

(2) The tolerable posture range of the second optimum posture is set to be narrower than the tolerable posture range of the first optimum posture. This allows for the specified user to measure the blood pressure with further stability and higher accuracy. The tolerable posture range for the fixed first optimum posture must be wide to be applicable to an unspecified user. Thus, the measurement accuracy for an unspecified user is lower than the measurement accuracy for a specified user. As a result, when the first optimum posture is used, the posture may differ for each measurement thereby increasing differences in the blood pressure measurement results. In contrast, the second optimum posture corresponds to a specific user (body built or the like of specific user) and has a tolerable posture range narrower than that of the first optimum posture. This decreases differences in the posture for each measurement and in the blood pressure measurement results.

(3) The liquid crystal panel 6, which serves as a display unit, includes the segment type display 6*a*, which is capable of displaying numerals that show the results of the blood pressure measured by the manometer 5. Thus, the user is notified of the blood pressure measurement result using the segment type display 6*a*, which is less expensive than a dot-matrix type liquid crystal panel. Further, the liquid crystal panel 6 includes the dot matrix display 6*c*, which is capable of graphically displaying the blood pressure measured by the manometer 5 with an array of dots. This allows for the blood pressure measurement results to be shown in a graph, which is communicated in a visual manner to the user and thereby easily understood. Additionally, the dot matrix display 6*c* functions as a communication unit, which communicates posture information to the user based on the comparison result of the posture detected by the detector 9 and the optimum posture stored beforehand. Thus, the dot matrix display 6*c* may be used to display graphics or the like and thereby communicate posture information in a visual manner to be easily understood. Further, the blood pressure measurement results (graph) and the posture information may be displayed on the same dot matrix display 6*c* when necessary (i.e., in accordance with the how the wrist sphygmomanometer 1 is being used). This allows for the liquid crystal panel 6 to be reduced in size (save space), while allowing for such information to be easily understood in a visual manner.

(4) The posture information communicated by the dot matrix display 6*c* includes guidance information for guiding the user to the optimum posture. This directly guides the user to the optimum posture. Position information, such as the user's posture relative to the optimum posture, may be displayed on the dot matrix display 6*c*. However, in such a case, the user would have to understand the positional relationship of the present posture and the optimum posture to contemplate the direction in which to change the posture so as to conform the user's posture to the optimum posture. In contrast, the illustrated embodiment displays guidance information on the dot matrix display 6*c*. Thus, by just following the displayed guidance information, the user may change his or her posture to the optimum posture.

The present examples and embodiments are to be considered as illustrative and not restrictive, and the invention is not to be limited to the details given herein, but may be modified within the scope and equivalence of the appended claims.

In the above-discussed embodiment, the tolerable posture range of the second optimum posture is narrower in the vertical direction than the tolerable posture range of the first optimum posture. However, the present invention is not limited in such a manner, and the tolerable posture range of the second optimum posture may be the same as the tolerable posture range of the first optimum posture.

In the above-discussed embodiment, the second storage section 10*b* is capable of storing the second optimum posture for two individuals (two specified users). However, the present invention is not limited in such a manner, and the second storage section 10*b* may store the second optimum posture for any other number of individuals such as one or three.

In the above-discussed embodiment, the display 6*a* or the display 6*b* may be changed to another type of a display such as a dot matrix type display or a liquid crystal panel. Further, the liquid crystal panel 6 includes the dot matrix display, which includes an array or matrix of dots to display the results of the blood pressure measured by the manometer 5 in a graph. However, the dot matrix display 6*c* may be eliminated. That is, the communication unit may include just the LED 7. In this manner, the communication unit that communicates to the user the posture information based on the comparison of the posture detected by the detector 9 and the ideal posture stored beforehand is not limited to the dot matrix display 6*c* and may be another communication unit.

In the above-discussed embodiment, the communication unit includes the LED 7 (auxiliary communication unit), which assists communication of the posture information. However, the present invention is not limited in such a manner, and the LED 7 may be eliminated. As another alternative, in addition to or in lieu of the LED 7, another communication unit may be used as the auxiliary unit. For example, as shown by the broken lines in FIG. 2, a voice communication unit 20, which communicates the posture information by generating speech output (e.g., "raise wrist"), may be used as such an auxiliary unit. The use of the voice communication unit 20 would communicate the posture information to a user in a manner that is easier to understand.

In the above-discussed embodiment, the dot matrix display 6*c* displays and communicates guidance information to guide the user to the optimum posture. However, based on the comparison of the posture detected by the detector 9 and the optimum posture stored beforehand, the dot matrix display 6*c* may display posture information other than the guidance information. For example, position information indicating the user's posture relative to the optimum posture may be displayed on the dot matrix display 6*c*. Alternatively, the position (height) of the wrist 2*a* at the optimum posture may be set as the reference position, and the dot matrix display 6*c* may display position information indicating whether the user's wrist 2*a* is located above or below the reference position. This allows the user to understand the positional relationship of the optimum posture and the present posture (detected posture) so that the user can change his or her posture (move the wrist 2*a*) in order for the present posture to conform to the optimum position.

In the above-discussed embodiment, when the posture detected by the detector 9 differs from the optimum posture, the dot matrix display 6*c* communicates the guidance information by displaying an arrow (graphic). However, the present invention is not limited in such a manner. For example, the dot matrix display 6c may communicate the guidance information by displaying characters that are simple and displayable on the dot matrix display such as "UP" and "DOWN". Further, when the posture detected by the detector 9 conforms to the optimum posture, the dot matrix display 6c of the above-discussed embodiment communicates such a state by displaying the characters "OK". However, the present invention is not limited in such a manner. For example, the dot matrix display 6c may communicate such situation by displaying a graphic, such as a lateral bar shown in the vertically middle part of the dot matrix display 6c to indicate that the user no longer needs to move.

In the above-discussed embodiment, the memory 10 (result storage) stores the posture determination information, which is based on the posture detected by the detector 9, in association with the result of the blood pressure measured by the manometer 5. However, the present invention is not limited in such a manner, and the posture determination information does not have to be stored.

In the above-discussed embodiment, the height from the plane 21 on which the user's arm 2b is rested to the main body 4 (wrist 2a) is detected as the user's posture. However, instead of or in addition to such posture, a further posture may be detected as the user's posture. In such a case, the data of the optimum posture stored in the memory would have to be changed in accordance with the further posture, and the detector 9 must be capable of detecting the further posture.

The present examples and embodiments are to be considered as illustrative and not restrictive, and the invention is not to be limited to the details given herein, but may be modified within the scope and equivalence of the appended claims.

What is claimed is:

1. A wrist sphygmomanometer attachable to a user's wrist, the wrist sphygmomanometer comprising:
   an operation unit operable by the user;
   a manometer that measures blood pressure;
   a detector that detects the posture of the user;
   a storage that stores an optimum posture for the user;
   a comparator that compares the posture detected by the detector and the optimum posture stored beforehand in the storage to generate posture information, the posture information including posture determination information, which indicates whether or not the posture detected by the detector differs from the optimum posture, and guidance information, which advises the user so that the user's posture approaches the optimum posture;
   a communication unit that communicates the posture information to the user; and
   a setting unit that sets the optimum posture in the storage;
   wherein the storage includes a first storage section, which stores a fixed first optimum posture corresponding to an unspecified user, and a second storage section, which stores a second optimum posture corresponding to a specified user;
   the setting unit is capable of storing a value based on the posture detected by the detector as the second optimum posture in the second storage section in accordance with an operation of the operation unit;
   the second optimum posture has a tolerable posture range set to be narrower than that of the first optimum posture; and
   the comparator is capable of comparing the posture detected by the detector with the first optimum posture or the second optimum posture in accordance with an operation of the operation unit.

2. The wrist sphygmomanometer according to claim 1, further comprising:
   a display unit including:
   a segment type blood pressure display capable of displaying numerals indicating the result of the blood pressure measured by the manometer;
   a dot matrix display capable of displaying a graph with a plurality of dots to indicate the result of the blood pressure measured by the manometer;
   wherein the communication unit includes the dot matrix display, and the dot matrix display is capable of displaying the posture information.

3. The wrist sphygmomanometer according to claim 2, wherein the guidance information is displayed as a graphic formed by a combination of the dots.

4. The wrist sphygmomanometer according to claim 2, wherein the posture determination information is displayed as a character formed by a combination of the dots.

5. The wrist sphygmomanometer according to claim 2, wherein the dot matrix display is capable of selectively displaying the blood pressure measurement result or the posture information on the same dot matrix display.

6. The wrist sphygmomanometer according to claim 2, wherein the storage is capable of storing the posture determination information in association with the blood pressure measurement result; and
   the dot matrix display is capable of displaying the posture determination information at the same time as when the blood pressure display displays the blood pressure measurement result.

7. The wrist sphygmomanometer according to claim 1, wherein the communication unit includes a voice communication unit that generates speech output to communicate the posture information to the user.

8. The wrist sphygmomanometer according to claim 1, wherein the communication unit includes a light emitting diode that indicates whether or not the posture detected by the detector differs from the optimum posture.

9. The wrist sphygmomanometer according to claim 1, wherein the operation unit includes a switch indicating whether the user is the specified user or the unspecified user;
   when the switch indicates the unspecified user, the comparator is capable of comparing the posture detected by the detector and the fixed first optimum posture set in the first storage section to generate the posture information; and
   when the switch indicates the specific user, the comparator is capable of comparing the posture detected by the detector and the second optimum posture set by the setting unit in the second storage section to generate the posture information.

* * * * *